United States Patent
Baughman et al.

(10) Patent No.: US 8,444,412 B2
(45) Date of Patent: May 21, 2013

(54) ANCHOR APPARATUS FOR CLEAR PLASTIC ORTHODONTIC APPLIANCE SYSTEMS AND THE LIKE

(75) Inventors: David Baughman, Louisville, KY (US); Jack Fisher, Memphis, TN (US); John Sparaga, Anchorage, AK (US)

(73) Assignee: Bi-Corticle LLC, Louisville, KY (US)

( * ) Notice: Subject to any disclaimer, the term of this patent is extended or adjusted under 35 U.S.C. 154(b) by 220 days.

(21) Appl. No.: 12/659,508

(22) Filed: Mar. 11, 2010

(65) Prior Publication Data

US 2010/0239993 A1  Sep. 23, 2010

Related U.S. Application Data

(60) Provisional application No. 61/202,584, filed on Mar. 16, 2009.

(51) Int. Cl.
*A61C 3/00* (2006.01)

(52) U.S. Cl.
USPC ................................................ 433/6; 433/24

(58) Field of Classification Search
USPC ............... 433/6–7, 18–19, 22, 225, 167–176, 433/179–182, 24, 215; 411/401, 408, 411, 411/412; 606/300–329; 623/17.17; 24/694, 24/683, 685, 686; 128/859–862
See application file for complete search history.

(56) References Cited

U.S. PATENT DOCUMENTS

| | | | | |
|---|---|---|---|---|
| 1,799,469 | A | * | 4/1931 | Kent .............................. 433/177 |
| 3,304,610 | A | * | 2/1967 | Weissman ...................... 433/178 |
| 5,092,770 | A | * | 3/1992 | Zakula ........................... 433/172 |
| 5,417,692 | A | * | 5/1995 | Goble et al. ................... 606/311 |
| 7,959,439 | B2 | * | 6/2011 | Bulloch et al. ................ 433/173 |
| 2008/0026338 | A1 | * | 1/2008 | Cinader .......................... 433/29 |
| 2008/0044786 | A1 | * | 2/2008 | Kalili ................................ 433/6 |
| 2009/0036889 | A1 | * | 2/2009 | Callender ....................... 606/55 |

* cited by examiner

*Primary Examiner* — Yogesh Patel
(74) *Attorney, Agent, or Firm* — Nixon & Vanderhye PC (57) ABSTRACT

Anchor apparatus for a flexible and resilient clear orthodontic appliance constructed to be removably fitted over the teeth of a user by friction in a predetermined position. One or more first anchor devices are secured to the bone in the mouth of the user in a position to be adjacent to the orthodontic appliance when fitted over the teeth. The orthodontic appliance is constructed to removably engage the first anchor device or devices when the orthodontic appliance is fitted on the teeth in the predetermined position to removably secure the orthodontic device in the predetermined position. The orthodontic appliance may comprise one or more second anchor devices mounted thereon for removable engagement with the first anchor devices. The first and second anchor devices comprise female recessed portions or male heads that are complementary in shape to facilitate the removable engagement thereof.

14 Claims, 9 Drawing Sheets

ANCHOR APPARATUS FOR CLEAR PLASTIC ORTHODONTIC APPLIANCE SYSTEMS AND THE LIKE

CROSS-REFERENCES TO RELATED APPLICATIONS

This application claims the priority of Provisional Patent Application No. 61/202,584 filed on Mar. 16, 2009.

BACKGROUND OF THE INVENTION

1. Field of the Invention

The present invention relates to an anchor apparatus for a clear plastic orthodontic appliance and, more particularly, to such an anchor apparatus that enables the clear orthodontic appliance to be removably mounted on the teeth of a user in a predetermined accurate position without movement unless subjected to a predetermined removable force for eating, drinking, inspection or cleaning of the teeth.

2. Description of the Background Art

Clear plastic orthodontic appliance systems such as the INVISALIGN® system have several desirable advantages over braces such as increased comfort, durability, hygiene and aesthetics. Such systems are removably positioned on the teeth by friction with the resulting disadvantage that they may not be accurately positioned in place, are not anchored in position and thus may be moved inadvertently out of position if subjected to sufficient force. The clear orthodontic appliances of such systems are constructed to be removed from the teeth during eating, drinking, inspection or cleaning of the teeth, and for replacement by another modified clear orthodontic appliance. It is important, therefore, that such clear orthodontic appliances be accurately positioned and re-positioned on the teeth of a user and be removably retained thereon in the accurate position.

The new and improved anchor apparatus of the present invention enables clear orthodontic appliances to be accurately positioned in place, to be removably retained in position and to be loaded more heavily for improved orthodontic results, such that they are not inadvertently moved out of a predetermined accurate position.

BRIEF SUMMARY OF THE INVENTION

The anchor apparatus of the present invention comprises one or more temporary anchor devices (TADS) which are secured to the bone in the mouth adjacent to the teeth of the user, and the clear orthodontic appliance is constructed to be mounted on the teeth and snap-fitted on to the TADS so as to be accurately positioned on the teeth and removably retained thereon in the desired position. In one embodiment, each of the TADS may comprise a male head which snaps into a complementary female pocket on the clear orthodontic appliance or, alternatively, the TADS may comprise a female pocket and a mating male portion may be formed on the clear orthodontic appliance.

The mating portions on the TADS and the clear orthodontic appliance may be adjustable in one, two or three axes and/or may be spring-loaded to improve workability. The TADS may be constructed in accordance with the anchor devices disclosed in co-pending patent application Ser. Nos. 11/508,909, filed on Aug. 24, 2006, and 12/149,398 filed on Apr. 30, 2008.

DETAILED DESCRIPTION OF THE INVENTION

Figure 1:
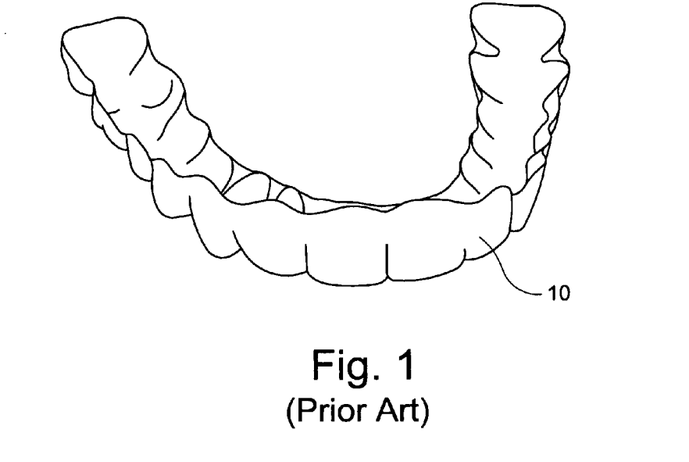
FIG. 1 is a perspective view of a conventional clear orthodontic appliance.
Figure 2:
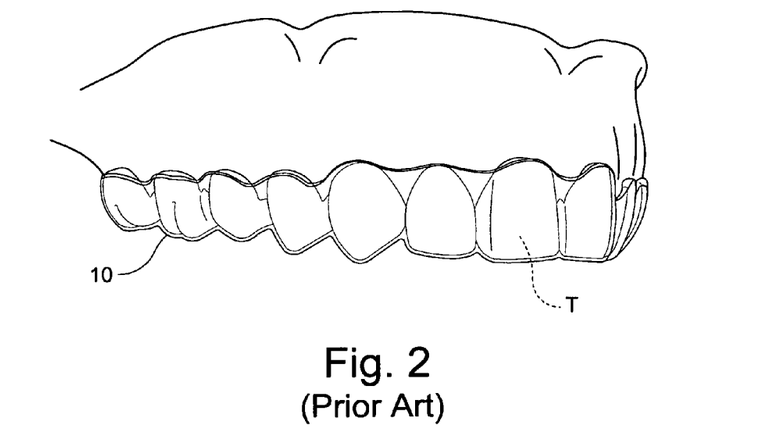
FIG. 2 is a perspective view of the clear orthodontic appliance of FIG. 1 mounted on the teeth of a user.
Figure 3:
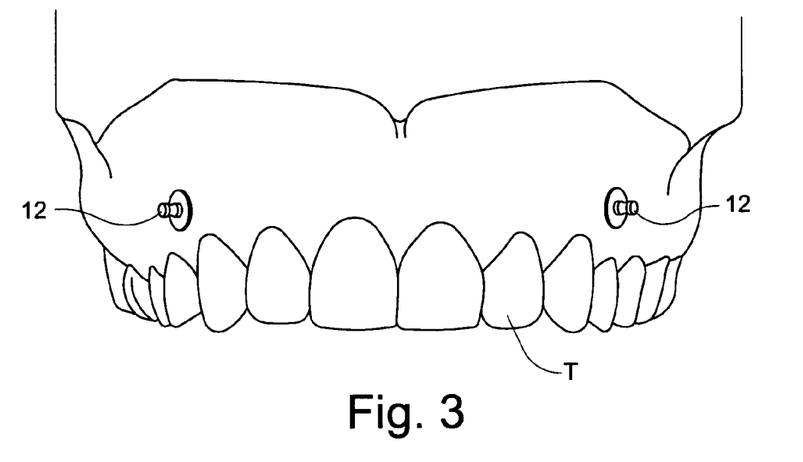
FIG. 3 is a front elevational view of the upper portion of a user's mouth showing the TADS mounted in the bone on opposite sides of the mouth above the teeth on which a clear orthodontic appliance is to be mounted.

FIGS. 1 and 2 illustrate the prior art wherein the clear orthodontic appliance 10 of FIG. 1 is constructed to be frictionally mounted on the teeth T shown in FIG. 2 in a removable manner such that it can be removed for eating, drinking, inspection or cleaning of the teeth T, and periodic replacement by modified clear orthodontic appliances. Because the orthodontic appliance 10 is frictionally mounted on the teeth T, it may not be accurately positioned and repositioned on the teeth and also is not anchored in position other than by friction and thus may move out of position if subjected to sufficient force.

Figure 5A:
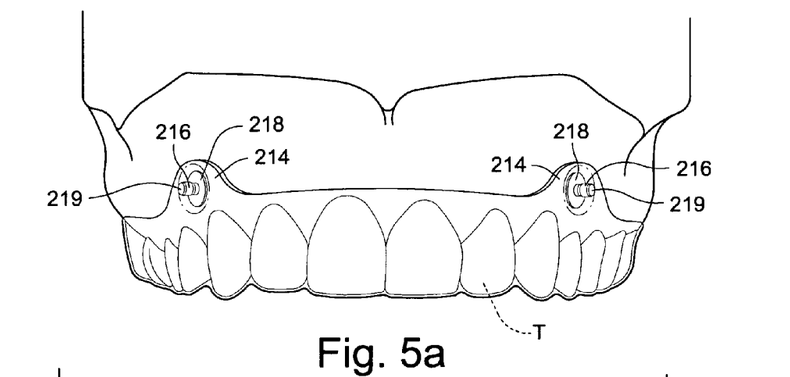
FIG. 5a is a perspective view showing the clear orthodontic appliance of FIG. 4a removably mounted on the teeth and TADS of FIG. 3.

FIGS. 3, 4a, 4b, 5a and 5b illustrate first embodiments of the present invention wherein TADS 12 are mounted in any suitable manner on opposite sides of the bone in the mouth adjacent to the teeth T and have male head portions of any desired or suitable shape. The clear orthodontic appliance 110 of FIG. 4a comprises raised flanges 14 on opposite sides thereof that have female mating portions 16 that are positioned to engage the TADS 12 when the clear orthodontic appliance 110 is mounted on the teeth T of FIG. 3, as shown in FIG. 5a, thereby removably retaining the orthodontic appliance in a desired accurate position on the teeth T. The female mating portions 16 may be integrally formed in the flanges 14 or may be formed in inserts of any suitable type secured to the flanges 14. The female mating portions 16 preferably have a shape that is complementary to that of the head portions of the TADS 12 such that they can be conveniently engaged and disengaged.

Figure 4A:
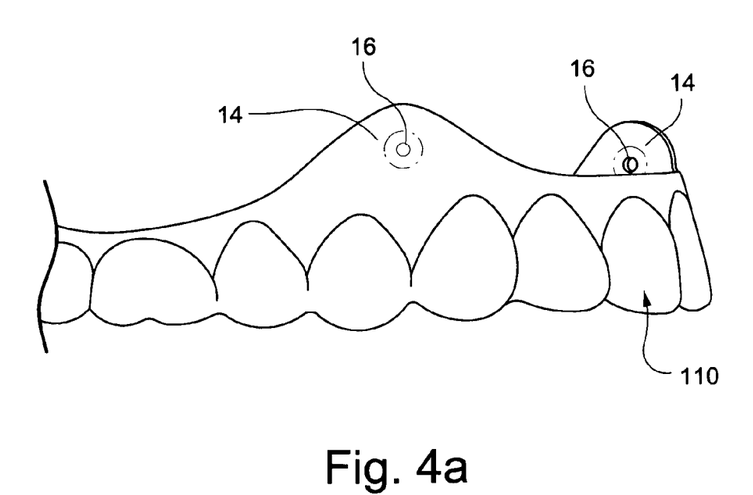
FIG. 4a is a perspective view of a clear orthodontic appliance constructed in accordance with the principles of the present invention.
Figure 4B:
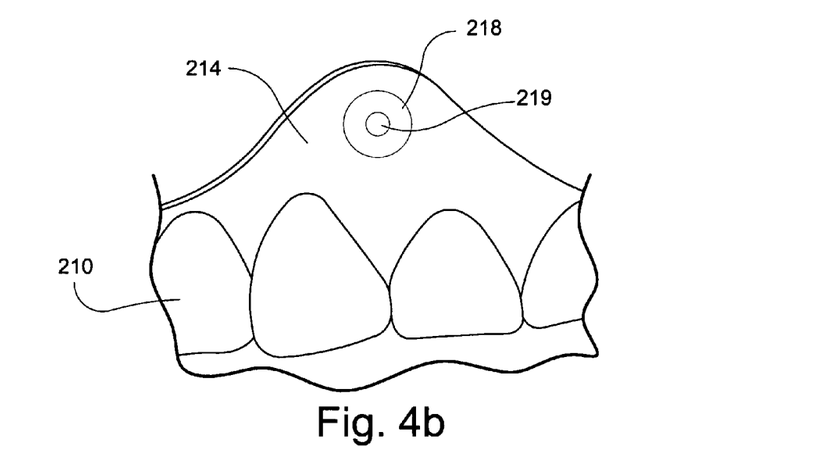
FIG. 4b is an enlarged perspective view like FIG. 4a showing a portion of a modified clear orthodontic appliance.
Figure 5B:
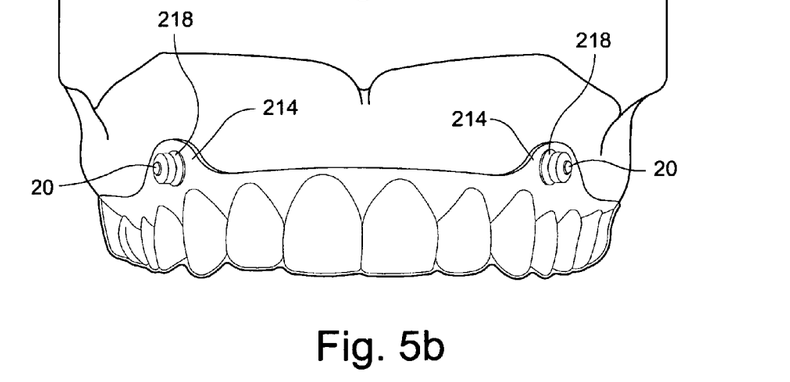
FIG. 5b is a perspective view showing the clear orthodontic appliance of FIG. 4b mounted on the teeth and TADS of FIG. 3.

FIG. 4b discloses a modified clear orthodontic appliance 210 wherein each flange 214 has an o-ring insert 218 with a central opening 219 that is adapted to removably receive the head portion of the adjacent TAD 12 when the clear orthodontic appliance is mounted on the teeth, as shown in FIG. 5b. To insure that each o-ring is the right size for the TAD 12 and the orthodontic appliance 210, the o-ring may first be removably mounted on the TAD and an impression made of the o-ring on the TAD. The flanges of the orthodontic appliance are then made using the impression so that the o-rings fit accurately and securely therein.

Figure 6:
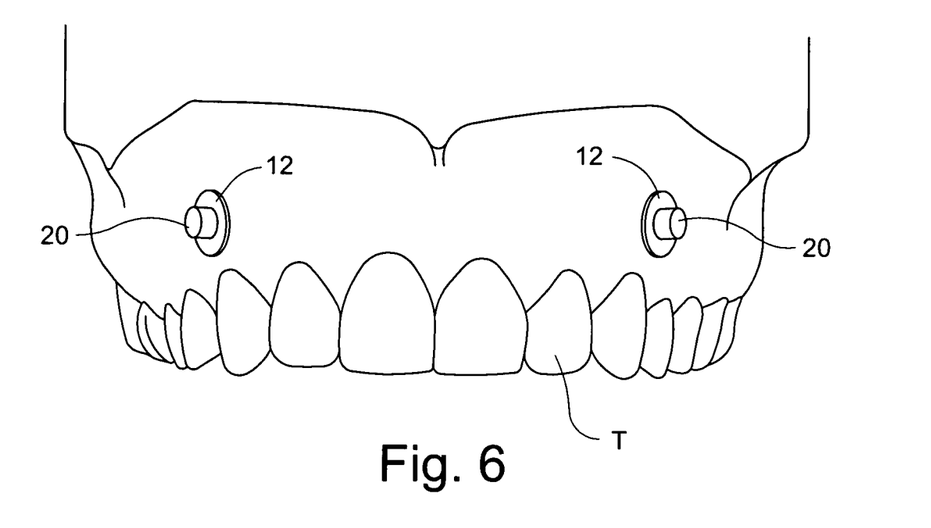
FIG. 6 is a front elevational view of the upper portion of the mouth similar to FIG. 3, showing enlarged heads or the like formed or mounted on the TADS.
Figure 7:
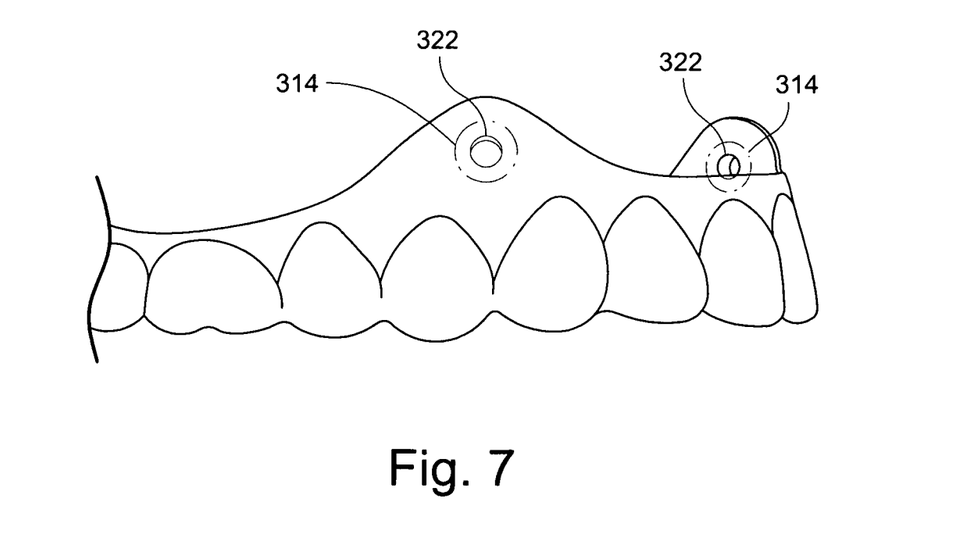
FIG. 7 is a perspective view of another embodiment of a clear orthodontic appliance constructed in accordance with the present invention.
Figure 8:
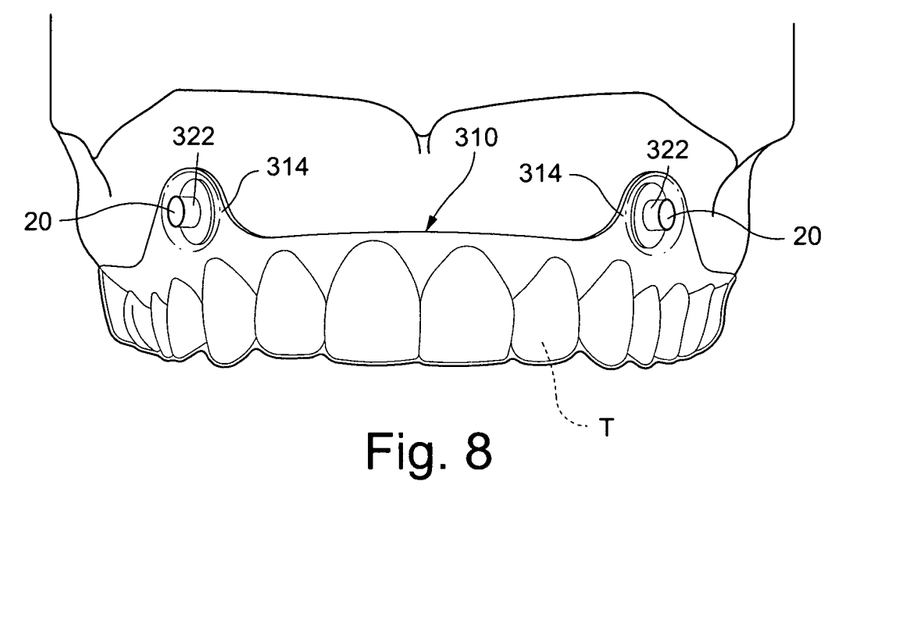
FIG. 8 is a perspective view showing the clear orthodontic appliance of FIG. 7 removably mounted on the TADS and teeth of FIG. 6.

FIGS. 6, 7 and 8 illustrate a further embodiment of the present invention wherein enlarged portions 20 are mounted on the heads of the TADS 12 and the flanges 314 of the clear orthodontic appliance 310 are provided with enlarged female mating portions 322 formed integrally therein or secured thereto having a size and shape complementary to that of the enlarged portions 20 such that they snap-fit over them when the orthodontic appliance 310 is mounted on the teeth T as shown in FIG. 8. Alternatively, the enlarged portions 20 may be integral parts of the TADS 12.

Figure 9:
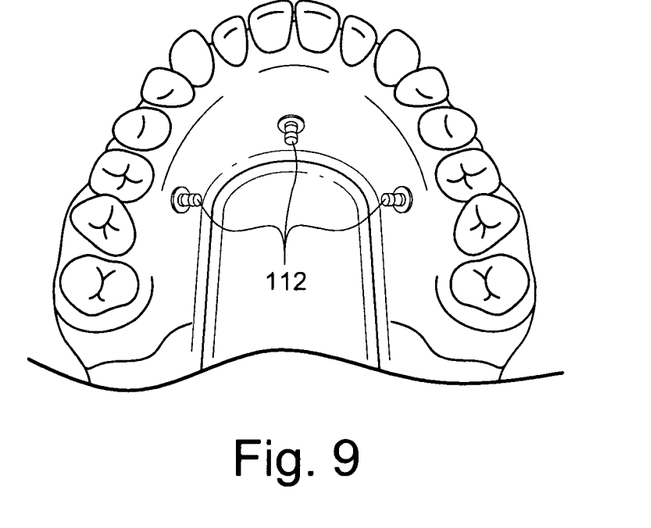
FIG. 9 is a plan view of one portion of the mouth showing TADS mounted on the bone adjacent to the teeth and extending into the inner area of the mouth.
Figure 10A:
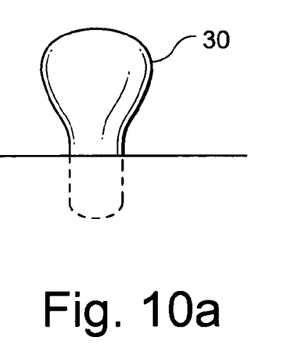
FIGS. 10a-10d are front elevational views, with parts broken away, of the outer ends of TADS with different illustrative head shapes that can be used in the apparatus of the present invention.
Figure 10B:
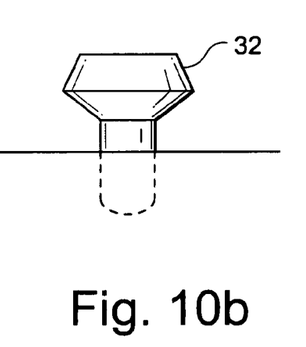
Figure 10C:
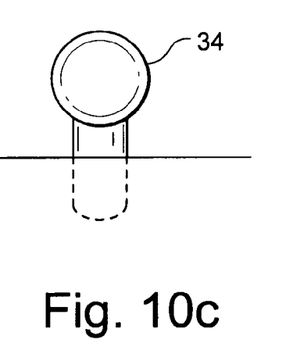
Figure 10D:
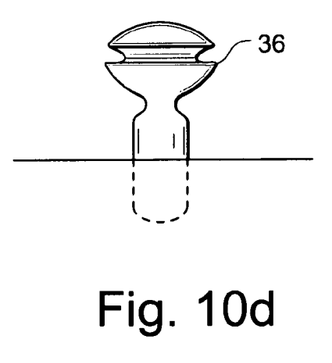

FIG. 9 illustrates a further modification of the present invention wherein the TADS 112 are secured to the bone on the inner portion of the mouth. In this embodiment, the flanges with female mating portions would be provided on the inner portion of the clear orthodontic appliance rather than on the outer portion thereof.

FIGS. 10a-10d illustrate examples of the male mating portions 30, 32, 34 and 36, respectively, of TADS that may be used in the present invention. In each case, the clear orthodontic appliance (not shown) would have flanges with female mating portions that would be complementary with the male mating portions.

Figure 11A:
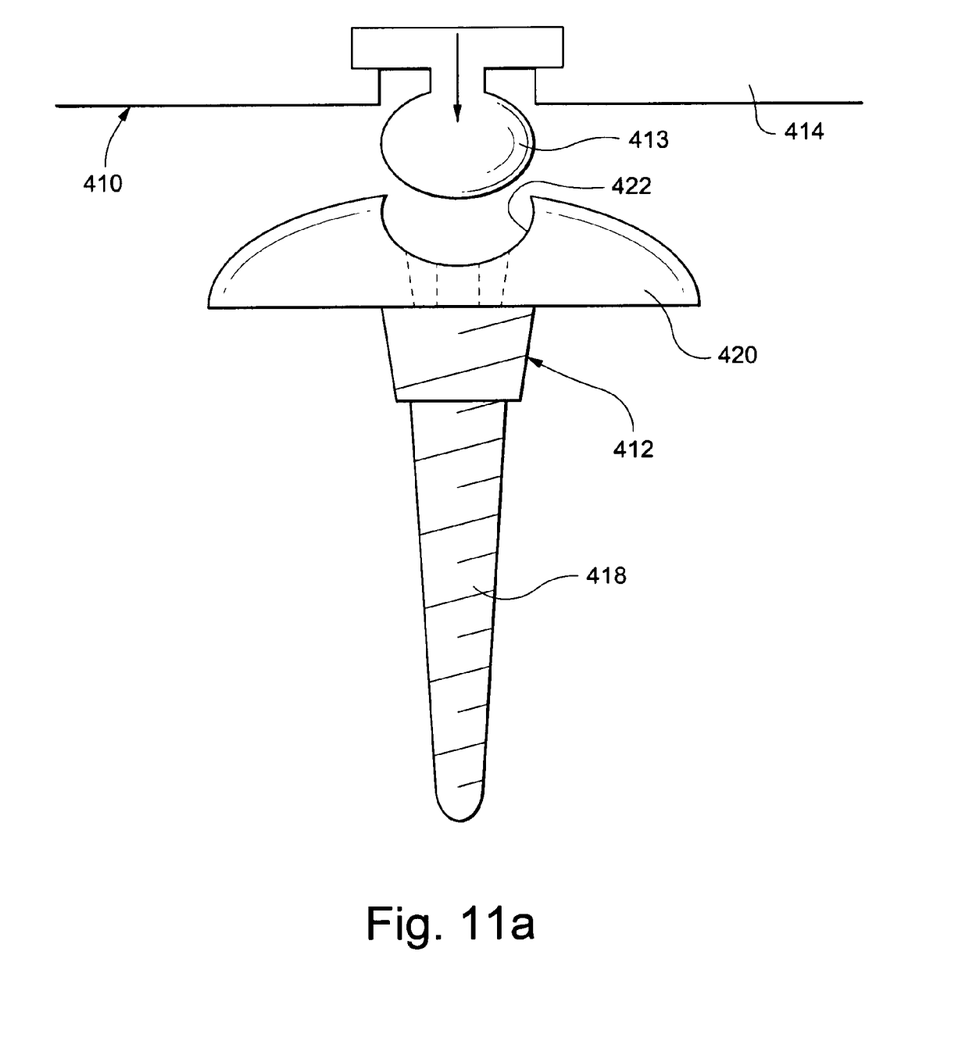
FIG. 11a is a front elevational view of a further embodiment of a TAD with a head having a female mating portion and a complementary male portion mounted on the clear orthodontic appliance.

FIG. 11a illustrates a further embodiment of the present invention wherein the flanges 414 of the clear orthodontic appliance 410 have a male mating member 413 of any suitable shape mounted thereon in any suitable manner. Each TAD 412 comprises an anchor portion 418 and a head portion 420 having a female mating portion 422 adapted to removably receive therein the male mating member 413 on the clear orthodontic appliance 410 for the purpose of positioning it accurately and anchoring it in the mouth so that it will remain in the desired position when subjected to loading or force.

Figure 11B:
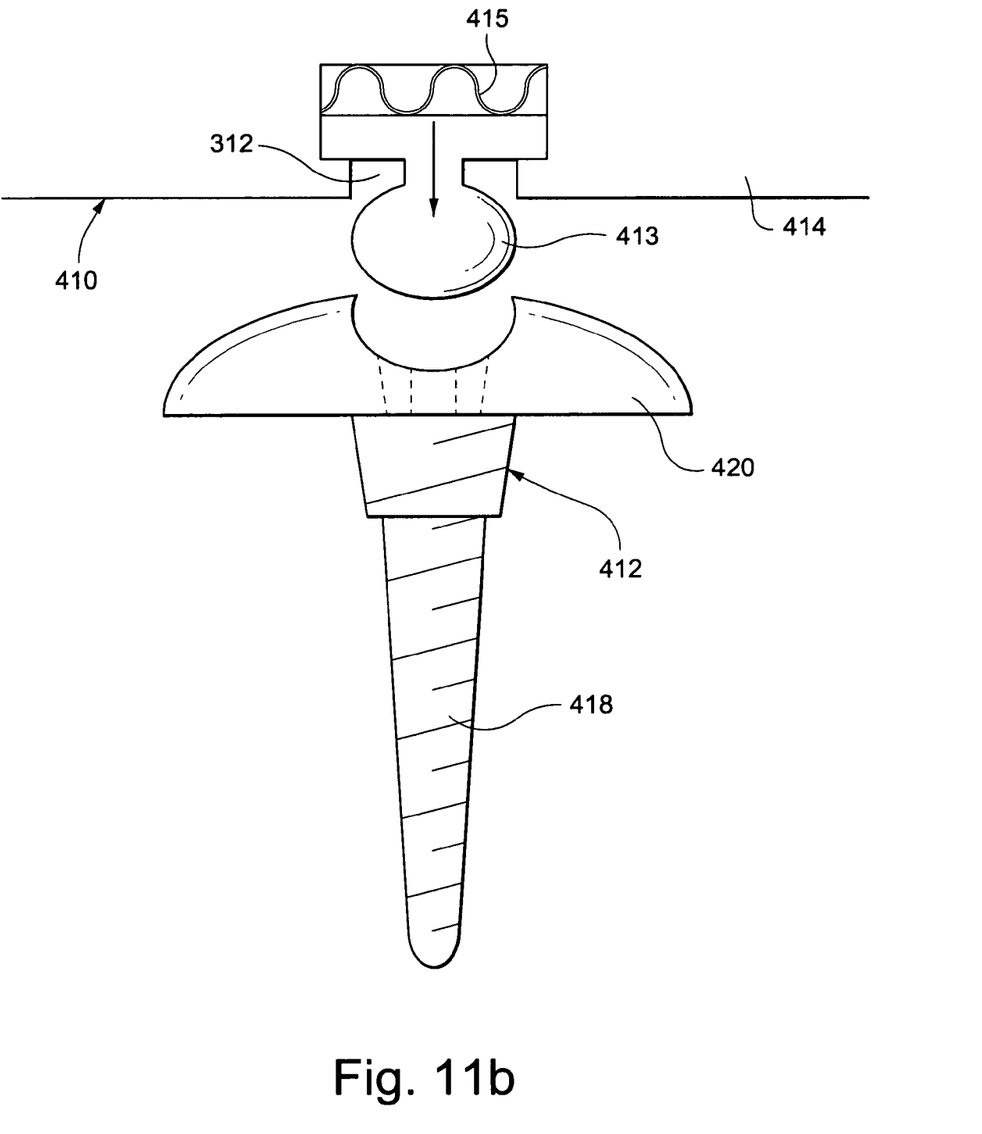
FIG. 11b is a front elevational view like FIG. 11a showing the male mating portion of the clear orthodontic appliance as being spring-loaded.

FIG. 11b discloses an embodiment similar to that of FIG. 11a wherein the male member 413 of the clear orthodontic appliance 410 is movably mounted on the flange 414 in engagement with a spring 415 so that it is spring-loaded.

Figure 12:
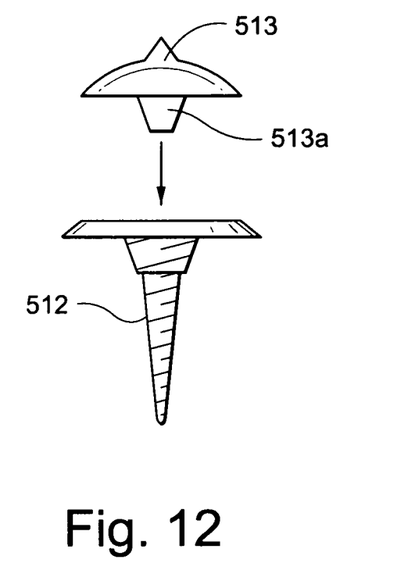
FIG. 12 is a front elevational view of a further embodiment of a TADS having a removable male head portion that can be mounted thereon in a predetermined orientation.

Another embodiment of a TAD 512 that can be used in the present invention is shown in FIG. 12 wherein the head portion 513 is removable from the TAD 512 and can be mounted thereon in a desired orientation by a self-locking tapered portion 513a. The head portion 513 may also be adjustably mounted on the TAD 512 to facilitate its removable engagement with the adjacent flange of the clear orthodontic appliance.

It will be readily seen from the foregoing description that the anchor apparatus of the present invention enables the expanded use of clear orthodontic appliances for the reason that they can be accurately removably positioned in place and subjected to greater forces which will shorten the period for orthodontic treatment.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A kit having a flexible and resilient orthodontic appliance constructed to be removably fitted over the teeth of a user by friction in a predetermined position, and anchor apparatus for the orthodontic appliance, said anchor apparatus comprising:

a first anchor device constructed to be secured to a bone in a mouth of a user in a position to be adjacent to the orthodontic appliance when fitted over the teeth, the orthodontic appliance being constructed to removably engage said first anchor device when the orthodontic appliance is fitted on the teeth of a user in the predetermined position, whereby the orthodontic appliance is removably secured in the predetermined position by said first anchor device, wherein said first anchor device comprises a female recessed portion and the orthodontic appliance comprises a male head portion that removably engages said female recessed portion when the orthodontic appliance is in the predetermined position.

2. The kit of claim 1 wherein said male head portion snap-fits over said female recessed portion in said first anchor device when the orthodontic appliance is in the predetermined position.

3. The kit of claim 1 wherein said male head portion is part of a second anchor device mounted on the orthodontic appliance.

4. The kit of claim 1 wherein the orthodontic appliance comprises a flange portion extending outwardly from a portion of the orthodontic appliance constructed to be fitted on the teeth when the orthodontic appliance is in the predetermined position, said male head portion being mounted on said flange portion to removably engage said female recessed portion when the orthodontic appliance is in the predetermined position.

5. The kit of claim 1 wherein a plurality of first anchor devices are constructed to be secured in spaced relation to the bone in the mouth of the user in positions to be adjacent to the orthodontic appliance when fitted over the teeth.

6. The kit of claim 5 wherein a plurality of second anchor devices are mounted on the orthodontic appliance and are positioned to removably engage the first anchor devices as the orthodontic appliance is fitted on the teeth in the predetermined position.

7. The kit of claim 6 wherein the orthodontic appliance comprises spaced flange portions extending outwardly from a portion thereof constructed to engage the teeth of a user when in the predetermined position, and said second anchor devices are mounted on said flange portions for removable engagement with said first anchor devices as the orthodontic appliance is moved to the predetermined position.

8. The kit of claim 6 wherein said first anchor devices and said second anchor devices are complementary in shape to facilitate the removable engagement thereof.

9. The kit of claim 5 wherein said first anchor devices are constructed to be mounted on the bone in an outer portion of the mouth of the user and to extend outwardly therefrom.

10. The kit of claim 5 wherein said first anchor devices are constructed to be mounted on the bone in an inner portion of the mouth of the user and to extend inwardly therefrom.

11. The kit of claim 1 wherein said female recessed portion comprises a flexible and resilient o-ring adapted to be snap-fitted over the male head portion.

12. The kit of claim 1 wherein the male head portion has a removable head portion for replacement by another head portion of a different shape.

13. The kit of claim 1 wherein the male head portion is constructed to be adjustable.

14. A kit having a flexible and resilient orthodontic appliance constructed to be removably fitted over the teeth of a user by friction in a predetermined position, and anchor apparatus for the orthodontic appliance, said anchor apparatus comprising:

a first anchor device constructed to be secured to a bone in a mouth of a user in a position to be adjacent to the orthodontic appliance when fitted over the teeth, the orthodontic appliance being constructed to removably engage said first anchor device when the orthodontic appliance is fitted on the teeth of a user in the predetermined position, whereby the orthodontic appliance is removably secured in the predetermined position by said first anchor device, wherein a plurality of first anchor devices are constructed to be secured in spaced relation to the bone in the mouth of the user in positions to be adjacent to the orthodontic appliance when fitted over the teeth, wherein a plurality of second anchor devices are mounted on the orthodontic appliance and are positioned to removably engage the first anchor devices when the orthodontic appliance is fitted on the teeth in the predetermined position, wherein said first anchor devices comprise male heads or female recessed portions, and said second anchor devices comprise female recessed portions or male heads, respectively, and wherein the male heads are spring loaded for removable engagement with the female recessed portions.

\* \* \* \* \*